US00PP21533P3

(12) United States Plant Patent
Pinochet

(10) Patent No.: US PP21,533 P3
(45) Date of Patent: Nov. 30, 2010

(54) **VARIETY OF *PRUNUS* ROOTSTOCK NAMED 'TEMPROPAC'**

(50) Latin Name: *(Prunus dulcis×P. persica)×P. persica*
Varietal Denomination: Tempropac

(75) Inventor: Jorge Pinochet, Barcelona (ES)

(73) Assignee: Agromillora Iberia, S.L., Barcelona (ES)

( * ) Notice: Subject to any disclaimer, the term of this patent is extended or adjusted under 35 U.S.C. 154(b) by 24 days.

(21) Appl. No.: 12/384,497

(22) Filed: Apr. 6, 2009

(65) Prior Publication Data

US 2010/0257645 P1 Oct. 7, 2010

(51) Int. Cl.
*A01H 5/00* (2006.01)

(52) U.S. Cl. ..... Plt./174

(58) Field of Classification Search ..... Plt./174

See application file for complete search history.

*Primary Examiner*—Annette H Para
(74) *Attorney, Agent, or Firm*—The Webb Law Firm

(57) ABSTRACT

A new and distinct hybrid peach plant used as a rootstock that exhibits red leaves, root-knot nematode resistance, and compatibility with peach, nectarine, and almond varieties.

4 Drawing Sheets

Botanical classification: (*Prunus dulcis×P. persica*)×*P. persica*.

Varietal denomination: 'Tempropac'.

BACKGROUND OF THE INVENTION

The present invention comprises a new and distinct cultivar of hybrid peach (*Prunus dulcis×P. persica*)×*P. persica* used as a rootstock known by the varietal name 'Tempropac' (experimental designation is PAC 9917-26). The new variety was discovered in Barcelona, Spain in 1999 as a result of a planned breeding program. The new variety is the result of a cross between 'Monegro' (*Prunus dulcis×P. persica*) (female parent, unpatented) and 'Flordaguard' *Prunus persica* (male parent, unpatented, public domain rootstock). The purpose of the breeding program was to develop rootstocks with low chilling requirements for peach varieties. The new variety exhibits similar red leaves and root-knot nematode resistance to both parents, but has a larger leaf size than both parents. Further, the new variety has similar chilling requirements to 'Flordaguard', but tolerates calcareous, alkaline soils better than its male parent, and the new variety's mature leaves turn green on the upper surface early in the season. The new variety has been trial and field tested and has been found to retain its distinctive characteristics and remain true to type through successive propagations. The following characteristics distinguish 'Tempropac' from other varieties known to the breeder:

1. Red leaves;
2. Early flowering;
3. No suckering;
4. Low chilling requirements;
5. Mature leaves are dark green on the upper surface and purple on the lower surface;
6. Flower stamens are dark pink to purple in color;
7. Mature leaves maintain a red toned petiole; and
8. Improved tolerance to salinity.

DESCRIPTION OF THE DRAWINGS

The accompanying photographic drawings illustrate the new variety with the color being as nearly true as is possible with color illustrations of this type.

DESCRIPTION OF THE PLANT

Figure 1:
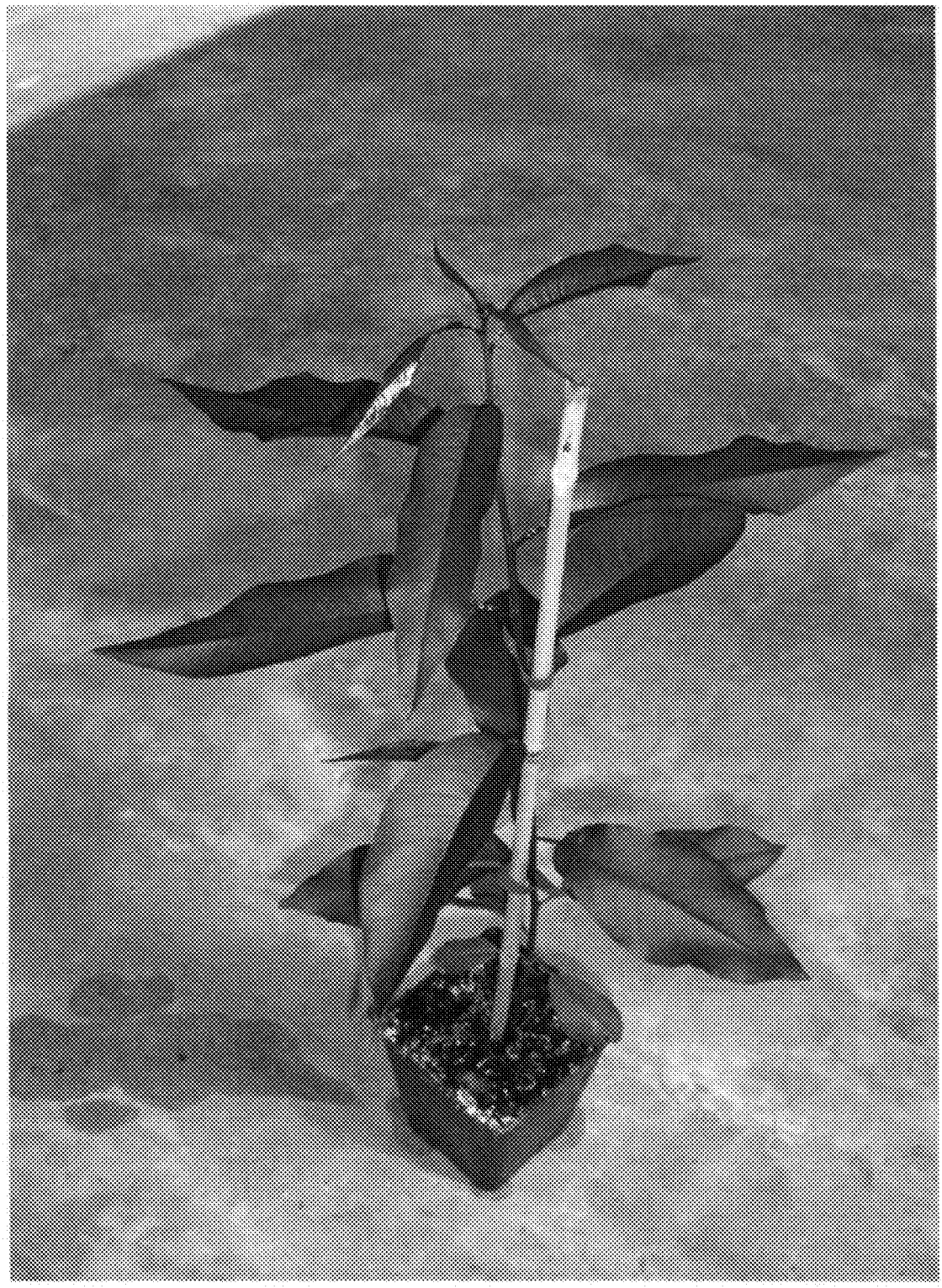
FIG. 1 shows an entire plant of the new variety.
Figure 2:
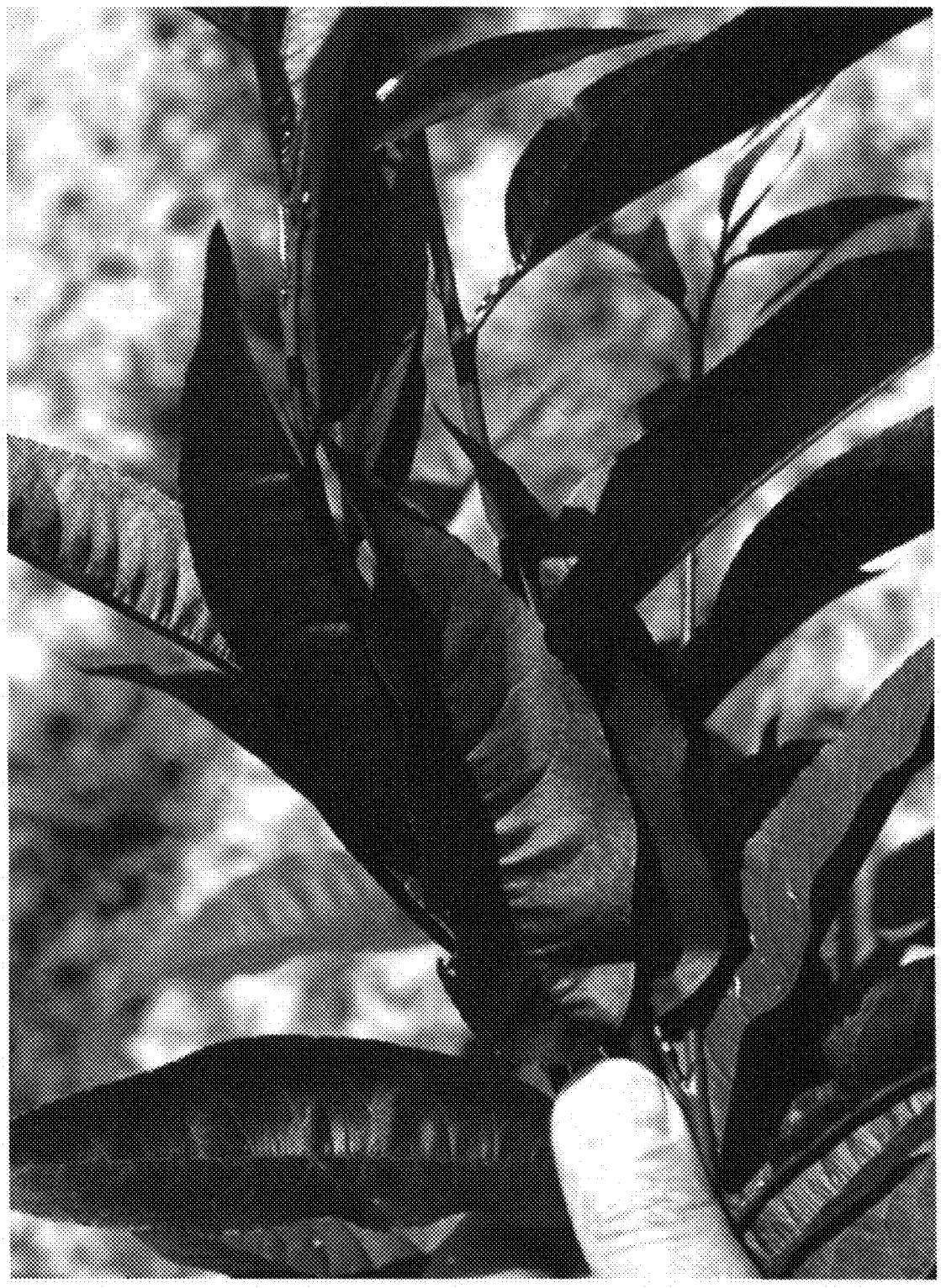
FIG. 2 is a close-up view of the mature leaves of 'Tempropac'.
Figure 3:
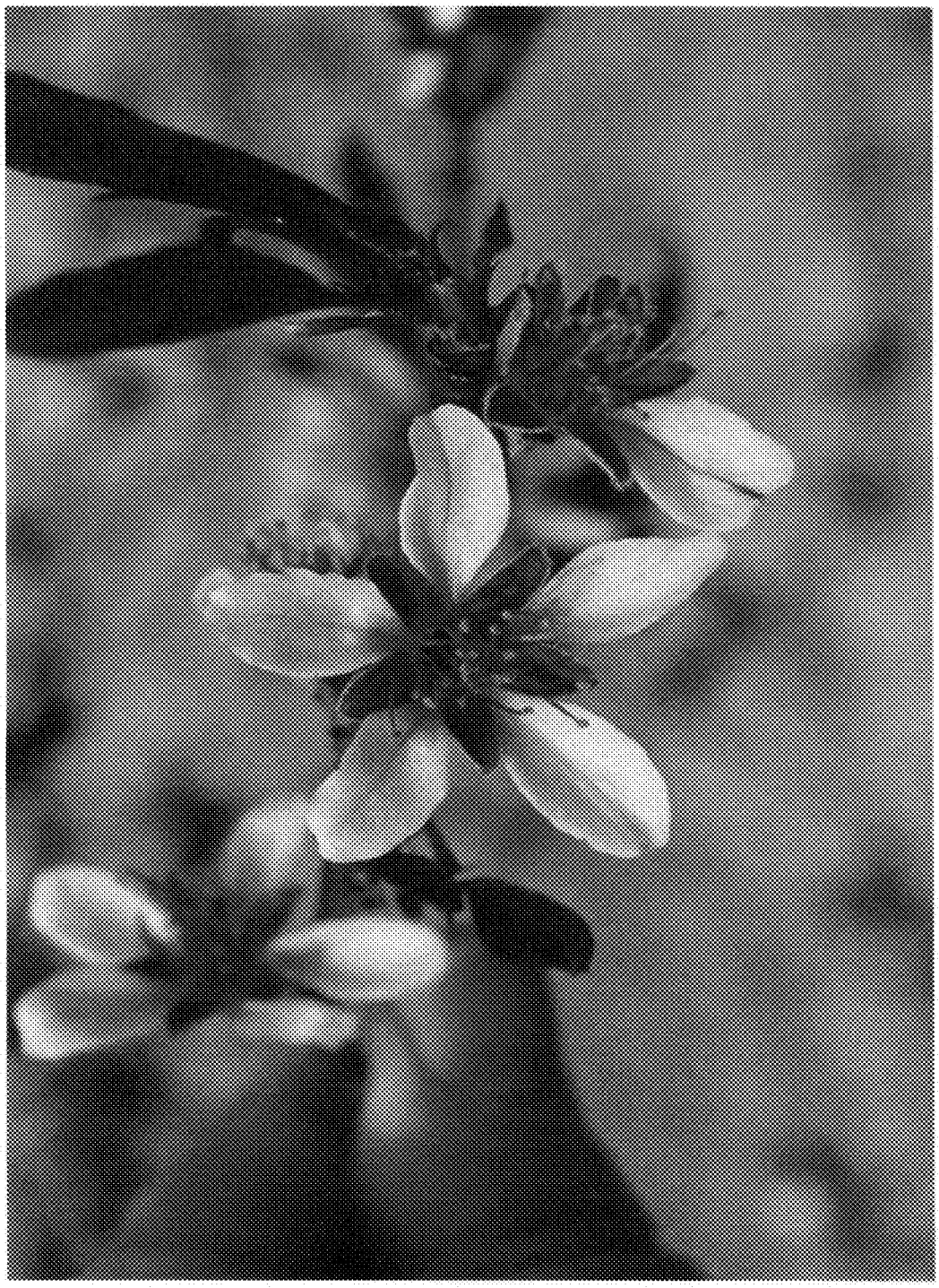
FIG. 3 is a close-up view of the flowers of the new variety.
Figure 4:
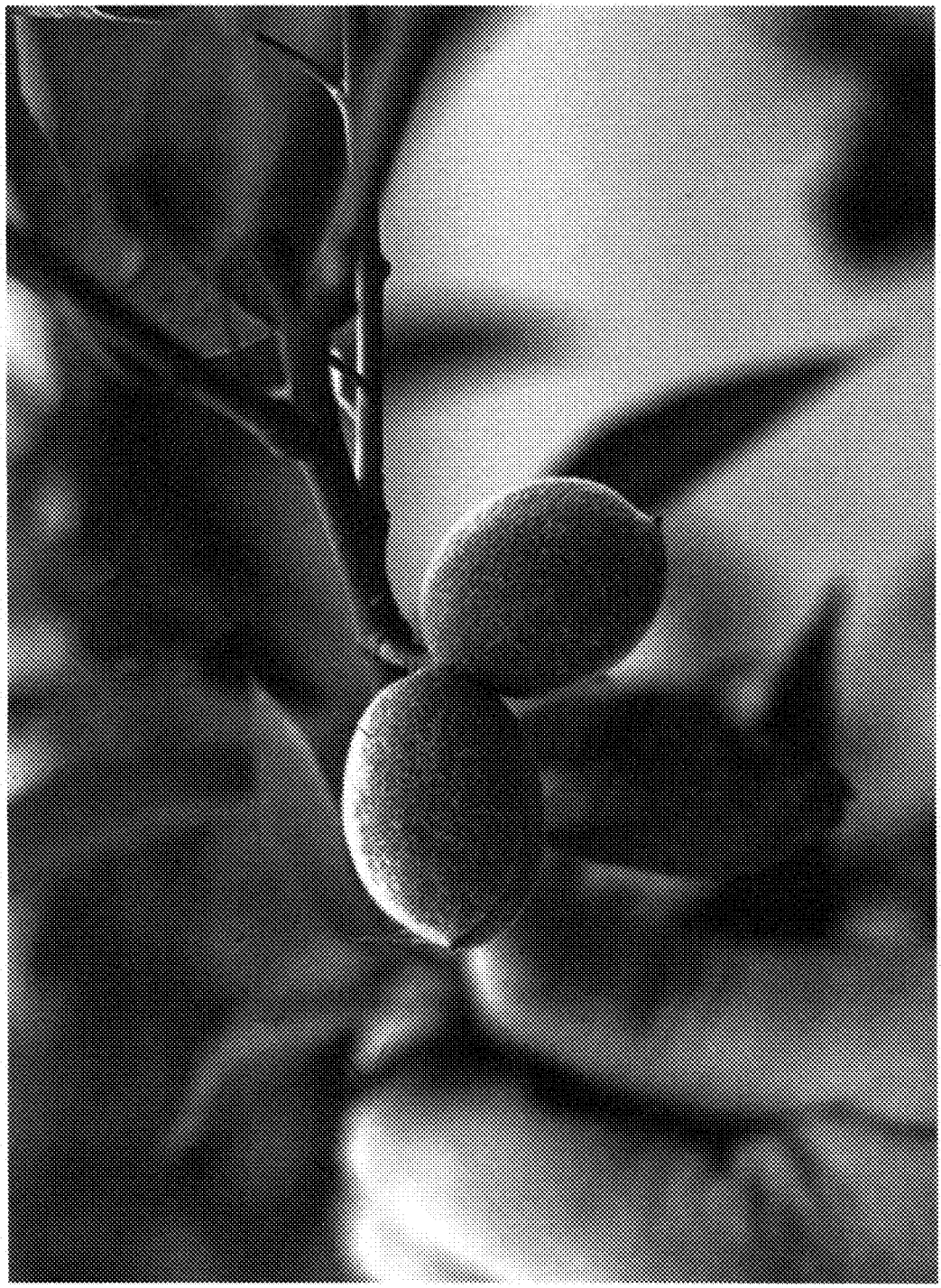
FIG. 4 is a close up view of the fruit the new variety.

The following detailed description sets forth the characteristics of the new cultivar. The data which defines these characteristics was collected under natural daylight on plants produced by asexual reproductions via in vitro propagation carried out in Barcelona, Spain. The plants were grown under normal field conditions. Color designations are presented with reference to the "Dictionary of Color" by A. Maerz and M. Rea Paul, Second Edition (1950).

TREE

Age: 7 years.
Size: 3.6 meters tall.
Vigor: Medium to high.
Density: Low.
Form: Semi-compact.
Production: Abundant.
Growth type: Upright spreading.
Bearing: Fruit bearing.
Pathogen resistance:
- *Fungal disease.*—Unknown.
- *Insects.*—Unknown.
- *Mites.*—Unknown.
- *Viruses.*—Unknown.
- *Other diseases.*—Root-knot nematodes (*Meloidogyne* spp.).

Rootstock performance:

*Root sprouts* (*suckering*).—Not present.

*Anchorage.*—Deep and spreading laterally.

*Compatibility.*—Compatible with peach, nectarine, and almond varieties.

*Vigor.*—Medium-high to high (similar to 'Nemaguard').

Trunk:

*Size.*—11 to 12 cm. in diameter.

*Surface texture.*—Smooth with slight scarfskin and large horizontal lenticels.

*Bark color.*—Plate 45, A 1 (Aluminum). The older the tree, the more ash-like the color.

*Lenticels.*—Length: 6 to 15 mm., oriented horizontally. Width: 1 to 2.5 mm. Color: Plate 6, A 1. Density: Medium.

Branches:

*Diameter.*—5 to 15 mm. (season's growth).

*Surface texture.*—Smooth with the current season with minor scarfskin as maturity advances.

*Color.*—Plate 7, E 10 (Chestnut) on the upper side of the branch and Plate 21, L 5 (Grass Green) on the lower side of the branch. Greenish-brown tones turn grayish-brown late in the season.

*Form.*—Circular in diameter.

*Average angle.*—Acute.

*Bud arrangement.*—Helicoidal throughout the branch.

*Lenticels.*—None present.

Leaves:

*Length.*—14 to 20 cm.

*Width.*—4 to 5 cm.

*Form.*—Lanceolate (elliptic); peach-like.

*Texture.*—Smooth and satiny on the upper surface.

*Thickness.*—Thin.

*Base.*—Right angled.

*Apex.*—Acute.

*Margin.*—Crenate.

*Pubescence.*—Upper surface: Absent. Lower surface: Absent.

*Color.*—Young leaves: Upper surface: Plate 7, L 7 (Maroon). Lower surface: Plate 7, J 6 (Garnet). Mature leaves: Upper surface: Plate 24, E 12 (Evergreen). Lower surface: Plate 8, L 8 (Brazil Brown).

*Petiole.*—Shape: Straight with a central groove along the top with large size nectaries near the base of the leaf. Length: 1.5 to 2 cm. Diameter: 2 mm. Color: Plate 7, J 5 (Tapestry Red).

*Veins.*—Venation type: Tree type disposition. Color: Upper surface: Plate 23, L 6 (Cypress Green). Lower surface: Plate 8, J 9 (Hindu Galleon).

Flower buds:

*Pedicel.*—Length: 0.5 mm. (barely noticeable). Diameter: 2 mm. Color: Plate 7, C 8, (Mauve Taupe).

*Bud.*—Length: 1.5 to 2.5 mm. Width: 1 to 2 mm. Shape: Ovoid and pointed. Color: Rapid variations in color tones from brown to gray; Plate 8, H 9 (Rembrandt) to Plate 16, A 6 (Taupe).

Flowers:

*Bloom timing.*—February 17th in Barcelona, Spain.

*Blooming period.*—10 to 15 days.

*Pollination requirements.*—None.

*Number of flowers per raceme.*—Individual.

*Fragrance.*—Medium to high (strong), rose-like.

*Petals.*—Number: 5. Length: 14 to 17 mm. Width: 7 to 9 mm. Shape: Elliptic. Aspect: Cupped upwards and inwards. Margin: Smoothly undulate. Texture and appearance: Smooth.

*Color.*—When opening: Upper surface: Plate 2, C 1. Lower surface: Plate 1, C 2 (Peach blossom). Fully opened: Upper surface: Plate 3, C 1. Lower surface: Plate 2, E 3.

*Sepals.*—Shape: Elliptic and pointed. Margin: Smooth. Texture: Pubescent. Length: 5 to 7 mm. Width: 3 to 5 mm. Color: Upper surface: Plate 8, L 5 (Zanzibar). Lower surface: Plate 7, L 8 (Mascara).

*Stamens.*—Number (per flower): 18 to 24. Filament length: 10 to 13 mm.

*Anthers.*—Shape: Kidney-shaped. Length: 1 mm. Color: Plate 13, H 7 (Yellow Beige).

*Pollen.*—Color: Plate 13, J 9 (Hazel). Amount: Abundant.

*Pistils.*—Length: 14 to 16 mm.

*Style.*—Length: 13 to 14 mm. Color: Plate 12, I 2 (Hay).

*Stigma.*—Shape: Flat and rounded. Color: Plate 12, J 6 (Honey Middlestone).

Fruit:

*Maturity when described.*—First week of August.

*Size.*—Diameter: 2 to 2.5 cm. Length: 3 to 4 cm.

Skin:

*Thickness.*—Thin.

*Texture.*—Smooth and pubescent.

*Tendency to crack.*—Not present.

*Color.*—Plate 7, J 9 (Tanagra).

*Ground color.*—Uniform.

Flesh:

*Aroma.*—Very weak.

*Color.*—Plate 19, I 1 (Butterfly).

*Texture.*—Hard.

*Eating quality.*—Leathery-type (not good).

Seeds:

*Number per fruit.*—One.

*Length.*—1.8 to 2.3 cm.

*Breadth.*—1.2 to 1.5 cm.

*Form.*—Wide and elliptic.

*Color.*—Plate 14, D 7 (Adobe).

Stem:

*Length.*—Variable.

*Width.*—3 to 7 mm.

*Color.*—Plate 8, L 7 (Carbuncle).

Use: As a rootstock for peach, nectarine, and almond varieties.

Winter hardiness: Hardy (under the conditions in Spain).

Bud winter hardiness: Medium.

Drought tolerance: Moderately tolerant.

I claim:

1. A new and distinct variety of hybrid peach plant used as a rootstock, as illustrated and described herein.

* * * * *